United States Patent
Wei

(10) Patent No.: US 10,692,590 B2
(45) Date of Patent: *Jun. 23, 2020

(54) METHOD FOR CONDUCTING ADAPTIVE CLINICAL TRIAL WITH DRUG DELIVERY DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/471,035

(22) Filed: Mar. 28, 2017

(65) Prior Publication Data

US 2017/0300665 A1 Oct. 19, 2017

Related U.S. Application Data

(60) Provisional application No. 62/323,214, filed on Apr. 15, 2016, provisional application No. 62/325,563, filed on Apr. 21, 2016.

(51) Int. Cl.
*G16H 10/20* (2018.01)
*G06F 19/00* (2018.01)

(52) U.S. Cl.
CPC ......... *G16H 10/20* (2018.01); *G06F 19/3456* (2013.01)

(58) Field of Classification Search
CPC ............................ G16H 10/20; G06H 19/3456
See application file for complete search history.

(56) References Cited

U.S. PATENT DOCUMENTS

| | | | | |
|---|---|---|---|---|
| 9,675,753 | B2 * | 6/2017 | Stempfle | A61M 5/1456 |
| 9,808,577 | B2 * | 11/2017 | Nagar | A61M 5/14244 |
| 2004/0107084 | A1 * | 6/2004 | Arakelyan | G06F 19/3456 |
| | | | | 703/11 |
| 2015/0144793 | A1 * | 5/2015 | Whalley | G01F 23/284 |
| | | | | 250/345 |
| 2015/0174209 | A1 * | 6/2015 | Chiquette | A61K 38/22 |
| | | | | 514/6.4 |

OTHER PUBLICATIONS

Mould et al., "Adaptive Dosing Dashboard System for Fully Individualized Dosing Makes Finding the Right Dose Easy", https://www.hbs.edu/openforum/openforum.hbs.org/goto/challenge/precision-medicine/adaptive-dosing-dashboard-system-for-fully-individualized-dosing-makes-finding-the-right-dose-easy, Mar. 12, 2016.*

(Continued)

*Primary Examiner* — Matthew F Desanto
(74) *Attorney, Agent, or Firm* — Min Wei

(57) ABSTRACT

The method set out herein involves conducting adaptive clinical trial to develop parenteral therapeutic product with variable dose drug delivery devices. The method comprises using a variable dose drug delivery device to respond modifications during the adaptive clinical trial, wherein the variable dose drug delivery device is able to deliver more than one dose level and is for delivering fluid formulation. Other methods set out herein involve using a variable dose drug delivery device equipped with radio frequency identification (RFID) or near field communication (NFC) technology to improve patient adherence to drug administration in the adaptive clinical trial.

18 Claims, 7 Drawing Sheets

(56) References Cited

OTHER PUBLICATIONS

Mould et al., Adaptive Dosing Dashboard System for Fully Individualized Dosing Makes Finding the Right Dose Easy, Mar. 12, 2016. (Year: 2016).*

Spencer et al. Operational Challenges and Solutions with Implementation of an Adaptive Seamless Phase 2/3 Study, Journal of Diabetes Science and Technology, col. 6, Iss. 6, Nov. 2012 (Year: 2012).*

* cited by examiner

FIG. 7
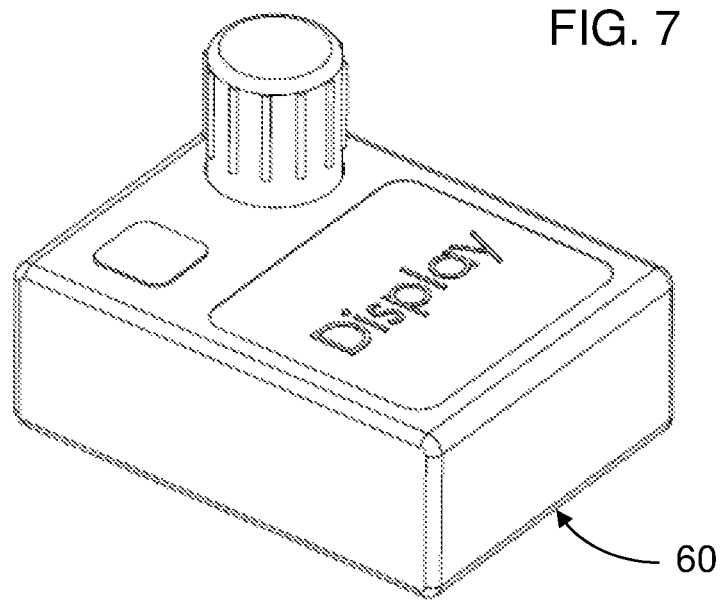
60
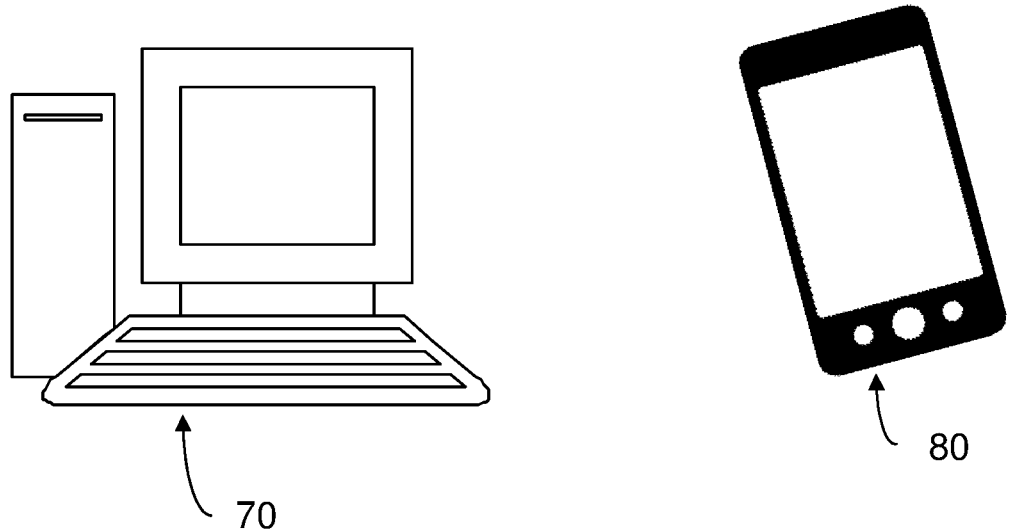
70
80

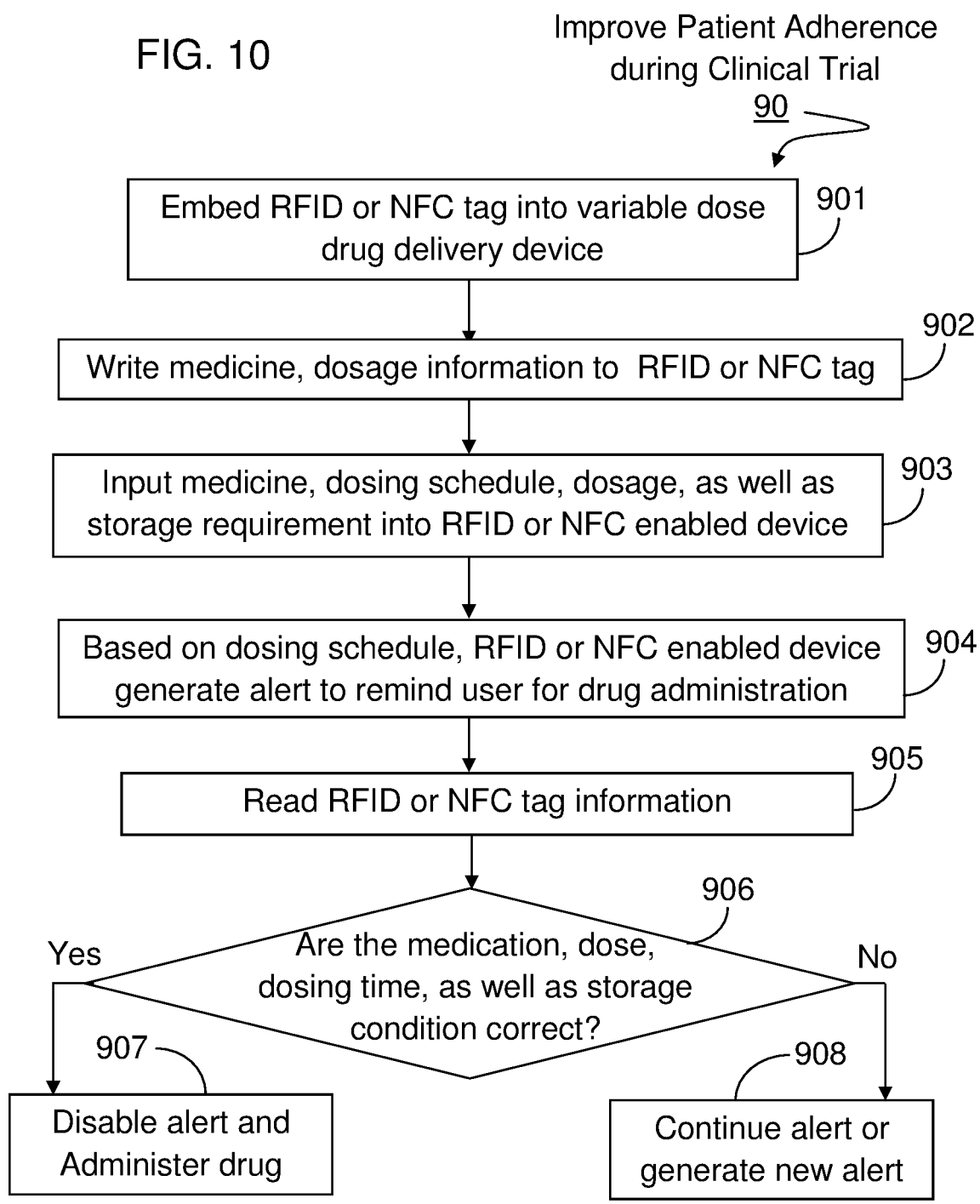

METHOD FOR CONDUCTING ADAPTIVE CLINICAL TRIAL WITH DRUG DELIVERY DEVICE

CROSS-REFERENCE TO RELATED APPLICATIONS

This application claims the benefit of U.S. Provisional Application Ser. No. 62/323,214, filed on Apr. 15, 2016 and U.S. Provisional Application Ser. No. 62/325,563, filed on Apr. 21, 2016.

BACKGROUND OF THE INVENTION

Adaptive designs have become popular in clinical trial and drug development. Unlike traditional trial designs, adaptive designs use accumulating data to modify the ongoing trial without undermining the integrity and validity of the trial, often incorporated with advanced mathematical modeling. As a result, adaptive designs provide a flexible and effective way to conduct clinical trials. The designs have potential advantages of improving the study power, reducing sample size and total cost, treating more patients with more effective treatments, identifying efficacious drugs for specific subgroups of patients based on their biomarker profiles, and shortening the time for drug development.

Although the benefits of adaptive clinical trials are advantageous, there are also challenges to conduct this type of flexible trials. First, the number of treatment doses in the adaptive dose-finding stage can be significantly more than traditional clinical trials. This scenario, with its potential treatment variability and additional provisioning to respond immediately to the adaptive changes, can inherently increase, by large amount, the quantities of study drug needed. For example, in order to shorten the clinical trial duration, an adaptive clinical trial had to prepare clinical drug supply by assuming all the patients in the trial will receive all different doses (total quantity of clinical supply=total number of patients×total number of different clinical dosages), which led to significant material wastage. Second, the study blinding for different dosages may become more complex when conducting adaptive clinical trials. Clinical trials of new drugs provide critical data on the drug's effectiveness, dosage requirements and possible adverse side effects. Unlike marketing strategies developed and applied to the introduction and sales of a new drug, it is desired and sometimes necessary in clinical studies to conceal or "blind" the drug to be studied. Blinding the clinical study is believed necessary to prevent bias from the participants—patients, investigators and sponsors—from comprising the results. Blinded studies can also enhance marketability of a product by more credibly demonstrating the favorable health and economic advantages, such as greater therapeutic efficacy and fewer adverse effects, when compared with a marketed drug or placebo. In addition, many governments require blinded clinical studies for approval of a new drug. (See 21 C.F.R. 314.26 and European Union's Directive 91/507/EEC). Effective blinding requires each aspect of the treatment—dosage form, packaging, labeling, dosage interval, dosage strength and dosage composition— to appear the same. That is, none of the participants to the study should be able to discern whether they are taking placebo, one or more strengths of investigational drug, or one or more strengths of comparator drug (the comparator or control drug is a marketed drug commonly used for the disease being studied). The blinding procedure is further complicated by the need to comply with all aspects of Good Manufacturing Practices (GMP) requirements. Third, the data generated in adaptive clinical trial are dynamic, there is currently no efficient way to capture the real-time clinical data and process the data for the next step of clinical trial. Patients will be dynamic members in the clinical trial. By far most of clinical trials today are led without direct information from patients as most information are gathered by human services suppliers amid patient visits. In any case, billions of individuals are as of now conveying associated individualized computing devices and billions more will be associated through wearable devices soon. This gives the chance to catch information specifically from patients in a continuous and convenient way as they enter that data on their own devices. Even better, information for non-transferable ailments, for example, hypertension and diabetes can be caught and transmitted straightforwardly through wearable medicinal sensing devices. Accordingly, the information caught will be significantly more point by point and of higher quality in this manner expanding the pace and viability of adaptive clinical trials.

In the future, clinical trial will be more precise and more personalized. Clinical trial systems will consistently facilitate all parts of the trial and investigational item progressively empowered by the Internet of Thing (IoT) base. Clinical trial systems will move into the cloud and will be able to correspond with individuals, different frameworks, devices and supplies by means of backing of standard conventions and personality administration.

Nowadays, biologic drugs account for more than half of all therapeutic drug candidates in pharmaceutical development pipelines. These biologic drugs need to be delivered in liquid or suspension formulations through the parenteral route. Drug delivery devices, including autoinjector and wearable infusors, have been widely used for delivering drugs in liquid or suspension formulations. These drug delivery devices can improve dose accuracy and ease medication preparation/administration and reduce needle injury, which results in more patient convenience and compliance. These type of devices can be powered by mechanical force, electromechanical force, powered gas or chemical reaction and so on. Meantime, these devices can, if designed properly, hide the difference in injection dose and can be a valuable tool in study blinding, while generating many different doses. Furthermore, these devices can be integrated with electronic circuits and the clinical data (dose, dosing time, etc) data can be recorded and communicated using embedded internet communication technology (for example, Bluetooth communication) for better scientific evaluation during the clinical trial. Therefore, these drug delivery devices are useful tools to control and record treatment signals during adaptive clinical trial.

Current autoinjector or infusor devices, as the most used automatic drug delivery devices for self-administering parenteral therapeutic drugs, are mostly designed for fix dose delivery and most of them don't have the ability to be connected with internet. These present following challenge to be used for clinical trial: difficult to conduct clinical trial when different doses are evaluated, for example, during the dose-finding clinical study. These challenges often delays the introduction of autoinjector or infusor device to clinical trial until the final dose is determined. Clinical trial is the most time consuming and most expensive part of drug development. Normally, all the three phases clinical trial together can take 5-8 years and cost hundreds of million dollars. During the long time period and with the substantial spending, there are a lot of learning about the drug, for example, when how the drug is absorbed, metabolized, and what the drug effect look like. On the other hand, when the parenteral therapeutic drug is developed together with the drug delivery device, there isn't much learning about the delivery device in the early phases of clinical trial, especially human factor and usability of the device, which is highly recommended by Food and Drug Administration (FDA) (FDA draft guidance—Applying Human Factors and Usability Engineering to Optimize Medical Device Design, 2011). Also, there is often no record about when and how the drug is taken. As mentioned above, in phase I and phase II clinical trials, a very important aspect is dose-finding, which requires devices that can deliver variable dose in adaptive clinical trial. Hence, the fixed dose drug delivery device is often introduced during very late stage of clinical trial. Currently, the clinical trial for parenteral therapeutic drug start with vial/manual syringe combination. Until phase III, the more sophisticated device, such as autoinjector or infusor will be introduced and studied. Or, the more sophisticated device will be evaluated after the first launch of the drug in vial/manual syringe format. Even then, the devices used normally doesn't have data communication functions. As the results, drug developers not only under-utilize the advantage of using autoinjector or infusor device in clinical trials, but also lose the opportunity to test device human factors and usabilities as well as collecting real-time usage data during the clinical trials.

Another important aspect about clinical trial is patient's adherence to drug administration. Adherence to clinically prescribed medications is essential for all effective clinical trial. Drug actions are inherently dose and time dependent, and as a result, variable underdosing diminishes the actions of trial medications. Poor adherence to medication is one of the major sources of variance in drug response and can confuse the interpretation of therapeutic efficacy in clinical trial and more so for adaptive clinical trial due the dynamic nature of adaptive clinical trial. Therefore, adherence to clinical prescribed medication, including timely initiation and accurate implementation of the dosing regimen throughout the specified period of clinical trial, is essential for the reliable evaluation of drug treatments and for the success of clinical trials. On the other hand, radio frequency identification (RFID) and near field communication (NFC) are effective technologies for reminding user and transmitting small data sets in real time. Also, these technologies consume very little or no energy and are ideal for clinical trials to evaluate parenteral medicines because these medicines often need to be stored in refrigerated environment. Utilizing these technologies in adaptive clinical trial can certainly enhance patient's adherence to clinical medicine prescribed.

In summary, what is needed is a new method for conducting adaptive clinical studies which permits for improved development of parenteral therapeutic products with drug delivery device during clinical trials.

SUMMARY OF THE INVENTION

Generally speaking, there is provided a method for improved use of clinical trials for developing parenteral therapeutic products. The method includes using variable dose drug delivery device for drug-administration during clinical trial phases. The ultimate goal of this method is to achieve optimal clinical outcome for all patient based on their individual characteristics. All the drug delivery devices presented here use pre-filled medication container for formulation in fluid state. Because the pre-filled dose form is easier to use for all people (much simpler preparation procedure and require less amount of professional training), including medical professionals who conducting clinical trials, there is no need to use the traditional lyophilized powder in vial unless the drug is unstable in the fluid formulation. With the variable dose drug delivery, it not only makes the randomization and blinding and clinical trial design become easier, but also simplify the clinical trial manufacturing because there is no need to produce too many drug doses in responding to the dynamic demand in adaptive clinical trial. It can be expected that large amount of resources will be saved with using the new method invented here. Moreover, because the drug delivery devices can be used and evaluated for a sufficient period of time during clinical trial, it provides plenty opportunities to collect detailed information about the human factor and usability information of the devices. It also provides opportunities to rapidly identify safety or operational signals requiring action to avoid significant and potentially costly issues such as adverse events and unnecessary delays. Furthermore, it will enhance patient adherence in clinical trials.

It is an object of the present invention to provide an improved method to develop parenteral therapeutic product with delivery device in adaptive clinical trial design.

It is also an object of the present invention to provide a clinical trial method to obtain optimal treatment for individual patients based on individual characteristics.

It is also an object of the present invention to provide a method for manufacturing clinical trial materials in a cost effective and more efficient manner.

It is also an object of the present invention to provide a method for conducting clinical trial with a device easy-to-use.

It is another object of the present invention to provide a method better for patient adherence.

Further objects and advantages of the present invention will become apparent from the following description of the preferred embodiment.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which:

FIG. 7 illustrates an example in that the information about drug administration dose, timing, and dosing rate using the variable dose drug delivery device is communicated through signal communication.

FIG. 10 illustrates example flow chart of managing drug administration with RFID enabled or NFC-enabled device.

DETAILED DESCRIPTION OF THE INVENTION

The present invention will become more fully understood from the detailed description given hereinbelow and the accompanying drawings which are given by way of illustration only, and thus, are not limitive of the present invention, and wherein:

The methods and apparatus presented herein can be used for conducting clinical trial to develop any of a variety suitable therapeutic agents or substances, such as a drug, into a patient. Initially it may be convenient to define that, the term "adaptive clinical trial" is meant to a clinical trial that allows modifications to the trial and/or statistical procedures of the trial after its initiation without undermining its validity and integrity; the term "variable dose drug delivery device" is meant to a drug delivery device capable of delivering at least two different doses; the term "fixed dose drug delivery device" is meant to a drug delivery device capable of delivering only one dose. The term "autoinjector" is meant to a device automatically delivering total dose within a short period of time, for example, less than 30 second. During the entire drug delivery period, user of the "autoinjector" is required to use hand to keep holding the device in place. The term "infusor" is meant to a device automatically delivering total dose within a long period of time, for example, more than 30 second. During the entire drug delivery period, user of the "infusor" is not required to use hand to keep holding the device in place all the time. The term "fluid" refers to either liquid or suspension.

Figure 1:
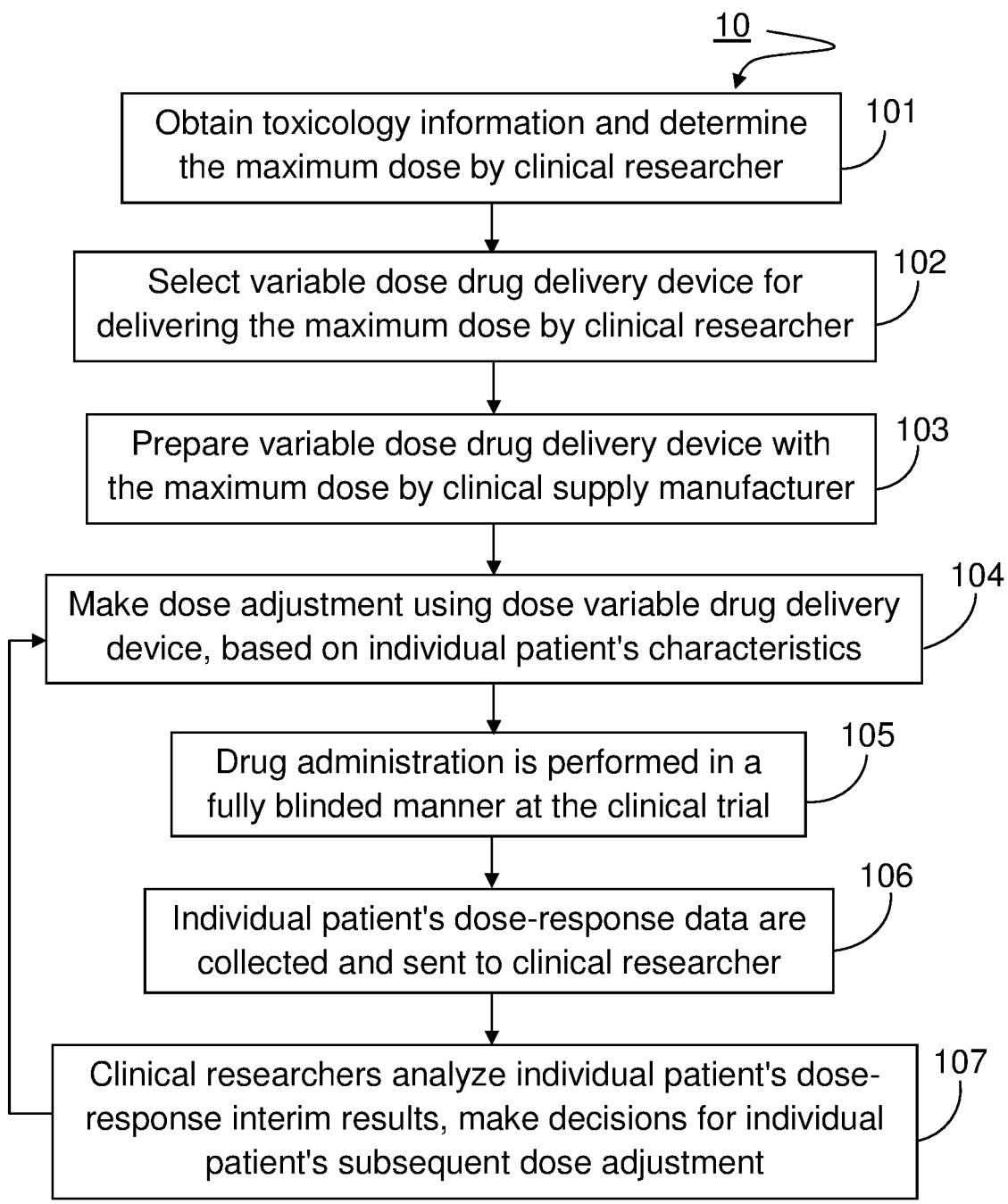
FIG. 1 illustrates a flowchart of an example method of conducting an adaptive clinical trial to evaluate drug performance, using variable dose drug delivery device.

FIG. 1 illustrates a block diagram of an example clinical trial method 10 configured to design and run at least one clinical trial. For brevity and conciseness, the following description will describe the execution of an example clinical trial to evaluate drug therapeutic performance. It should be noted that multiple clinical trials can be designed and executed, whether contemporaneously or sequentially, in a similar fashion described hereinafter.

The method 10 starts with operation 101 where drug developer conducts pre-clinical studies in animal models and phase I clinical studies in human subjects to obtain pharmacokinetics, pharmacodynamics and toxicology information in order to determine the maximum dose (for example, maximum tolerated dose, MTD). At operation 102, a variable dose drug delivery device, which will be used in clinical trial, is selected. Examples of these drug delivery devices are illustrated and explained with reference to FIG. 3-6. With knowing the maximum amount of drug and the formulation to be used, the maximum volume of the medication to be delivered is determined. Then, a decision needs to be made about whether the delivery will be a single bolus injection or an infusion, based on the patient's age, delivery site and the maximum volume of the medication to be delivered for clinical trial evaluation. For example, the maximum amount of medicine that is allowed to be delivered as a single bolus injection in thigh (vastus lateralis muscle) is 4 ml. If the maximum volume of the medication to be delivered for clinical trial evaluation is less than the maximum volume of the medication that can be delivered as single bolus injection at certain tissue site (4 ml for thigh), a variable dose autoinjector is selected for clinical trial studies. Otherwise, a variable dose infusor is selected for clinical trial studies. At operation 103, clinical supply manufacturer(s) prepare the variable dose drug delivery device with the maximum dose, according to the request from clinical researchers. The number of drug delivery devices prepared is equal to the total number of patients that will be enrolled into the clinical trial (sometime, small number of extra may be necessary for contingency). By this way, significant cost saving can be achieved. The table below shows an example.

TABLE 1

Comparison for clinical supply units needed with and without using variable dose drug delivery device

| Clinical dose level | Clinical supply units needed without using variable dose drug delivery device | Clinical supply units needed with using variable dose drug delivery device |
|---|---|---|
| 5 | 100 × 8 | 100 × 8 |
| 4 | 100 × 8 | 0 |
| 3 | 100 × 8 | 0 |
| 2 | 100 × 8 | 0 |
| 1 | 100 × 8 | 0 |
| Total Units | 4000 | 800 |

In this example, there are 100 patients enrolled in an adaptive clinical trial. The clinical researchers plan to evaluate 5 different dose levels. Each patient receives weekly treatment for 8 weeks. To ensure that the trials efficiently meet specific study objectives for all likely dose-response relationships (i.e. all possibilities will be tested in the clinical trial), if without using the variable dose drug delivery device, clinical supply manufacturer needs to prepare 800 clinical units for each dose level for the 8 week clinical trial duration. So, the total number of clinical units needed for this scenario is 4000. In contrast, if with using the variable dose drug delivery device, clinical supply manufacturer only needs to prepare 800 clinical units for all the 5 dose levels for the 8 week duration. The 800 variable dose drug delivery devices contain the maximum dose. Meantime, the drug formulation and filling volume in the medication container will be the same for all the different doses because of the variable dose drug delivery device used. In this example, rather than producing clinical trial units to cover all the possibilities ahead of the dynamic adaptive clinical trial, the invention herein utilizes variable dose drug delivery device that can vary doses dynamically to cover the possibilities during adaptive clinical trials. As the result, there are 3200 clinical units (or 80%) reduction in this example. If there are more dose levels or dose level combinations that need to be evaluated, the reduction will even more. For clinical trials, especially for clinical trials to test expensive biological drugs, the cost saving is significant. The clinical trial materials manufacturing and transportation and storage efficiency can also be greatly increased.

At operation 104, the dose setting for individual patient is conducted according to the request from clinical trial researchers. In the clinical trial, clinical trial researchers make decision for dosage based on treatment goal and individual patient's characteristics, including weight, age, gender, disease stage, genetic makeup, diet information, lifestyle, metabolize rate, etc. The dose setting can be accomplished by on-site adjustment to the variable dose drug delivery device, or through a dose adjusting equipment controlled remotely by clinical trial researchers. With using the clinical trial version of the variable dose drug delivery device, the difference in multiple doses in the dose-finding studies is blinded to the participants in the clinical trial. At operation 105, drug administration for each patient is performed in a fully blinded manner at the clinical trial site(s). Then, at operation 106, the drug-response data is collected and sent back to clinical researchers. Nowadays, the drug-response data can be collected in real time using various sensor technologies and the data can be sent to clinical researchers through internet communication. At operation 107, clinical trial researchers analyze individual patient's dose-response interim results, make decisions for individual patient's subsequent dose adjustment based on accumulated data. This can be done through advanced modeling, such as machine learning. Operation 104 to 107 are repeated until the clinical trial goal is reached. If the same process is applied on every patient enrolled in the trial, the right dose can be found for each individual and the study will be a N-of-1 clinical trial.

Figure 2:
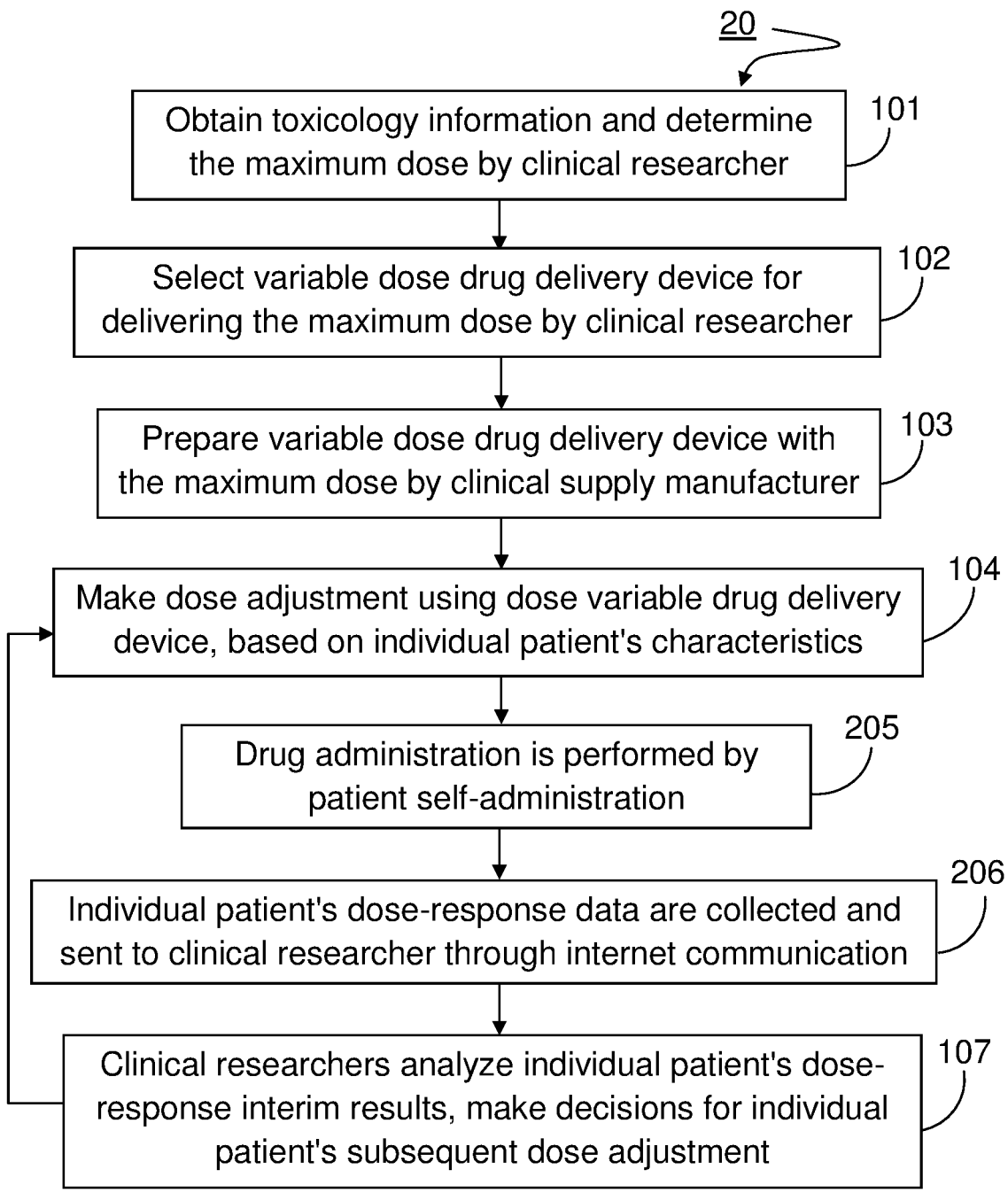
FIG. 2 illustrates a flowchart of another example method of conducting an adaptive clinical trial to evaluate drug performance, using variable dose drug delivery device.
Figure 3:
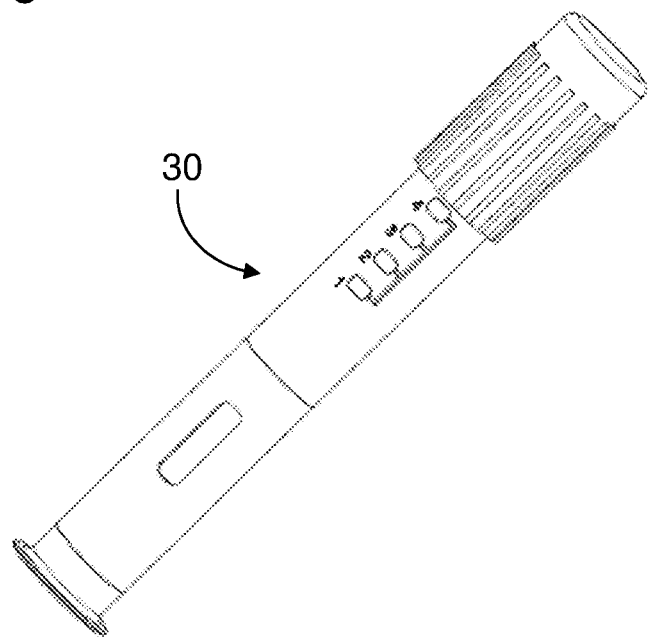
FIG. 3-6 illustrate example variable dose drug delivery devices.
Figure 4:
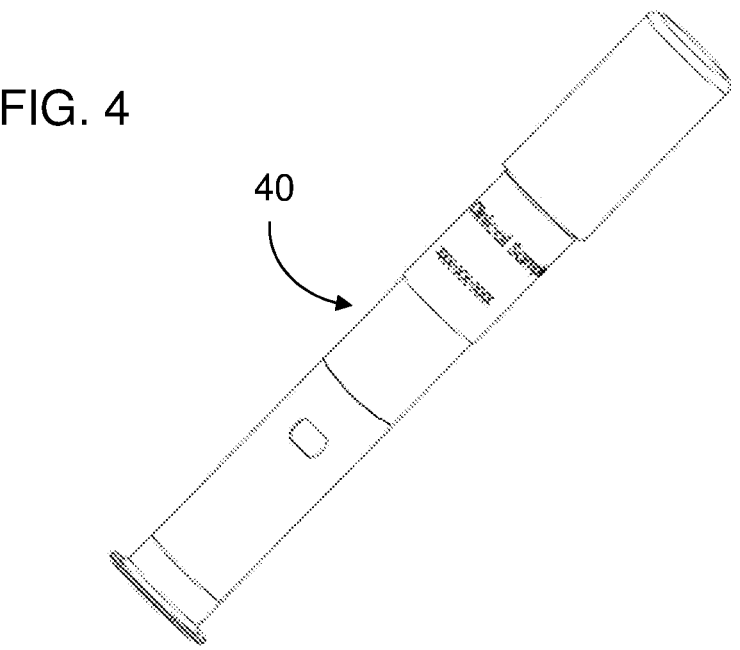
Figure 5:
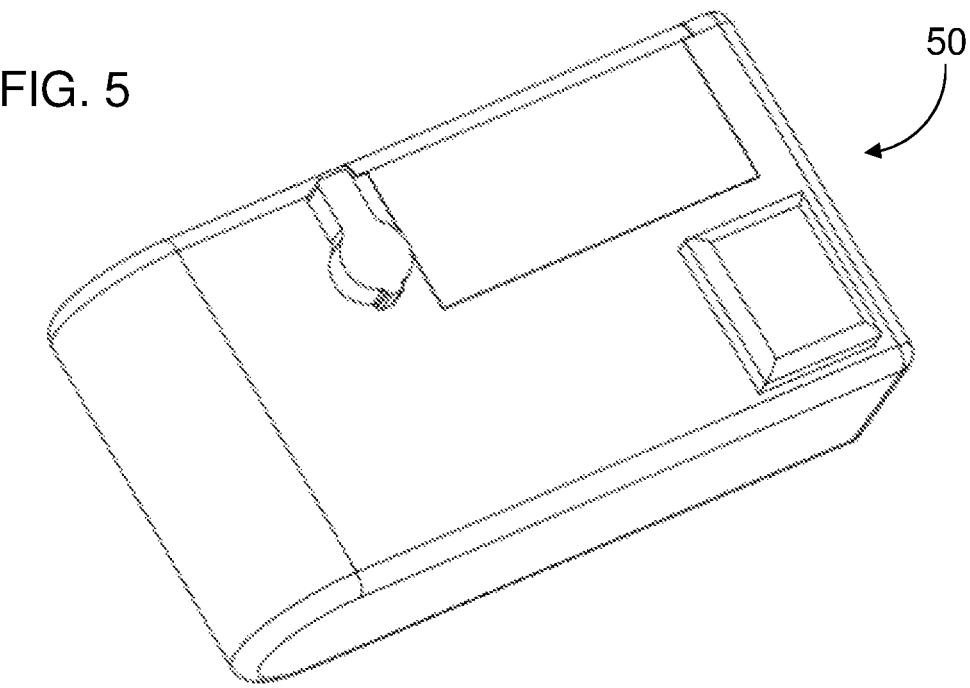
Figure 6:
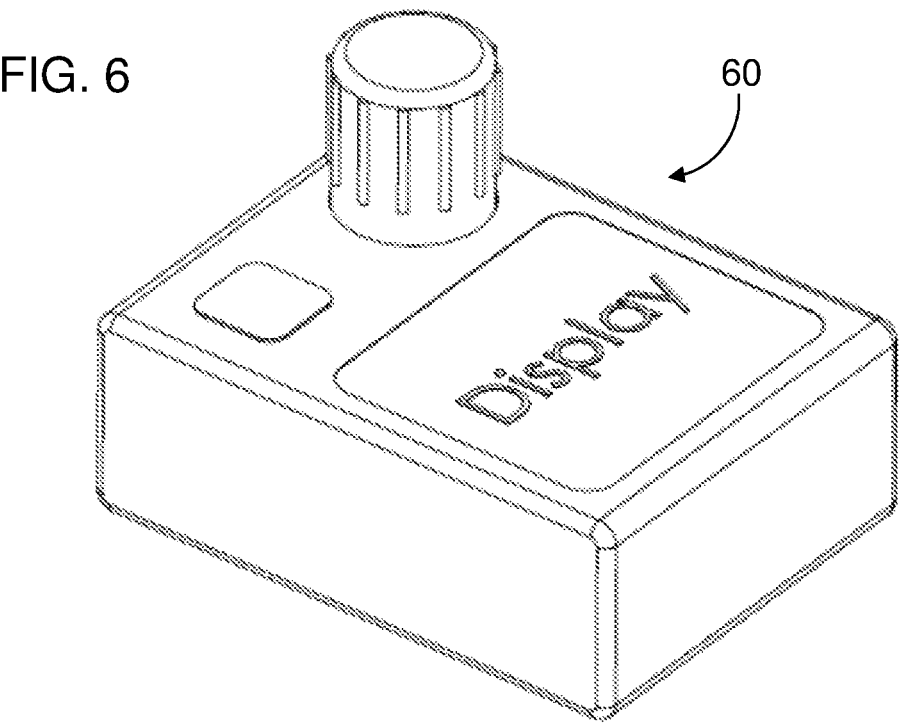

FIG. 2 illustrates a block diagram of another example clinical trial method 20 configured to design and run at least one clinical trial, according to this invention. The method 20 has similar operation procedure to the method 10. In the method 20, operation 205 and 206 are used to replace operation 105 and 106 in the method 10. In operation 205, drug administration is performed by self-administration in outpatient environment. In the outpatient environment, unlike in the clinical site, adherence to drug administration is critical for reliable clinical data. The method to improve drug administration adherence will be introduced later. At operation 206, individual patient's dose-response information are collected and sent to clinical researcher through internet communication. Again, the sensor technologies can help the dose-response data transmitted in a real-time manner.

FIGS. 3-6 illustrate examples of variable dose drug delivery devices (30, 40, 50 and 60) used in clinical trials according to the invention. The detail description of the functions of operation procedures of these variable dose drug delivery devices (30, 40, 50 and 60) is disclosed in US patent application US 2016/0092659, which is incorporated herein by reference.

FIG. 7 illustrates an example in that the information about drug administration dose, timing, and dosing rate using the variable dose drug delivery device 60 can be communicated through internet signal transmission between the device 60 and other information technology equipment, such as computers 70 or mobile devices 80.

Figure 8:
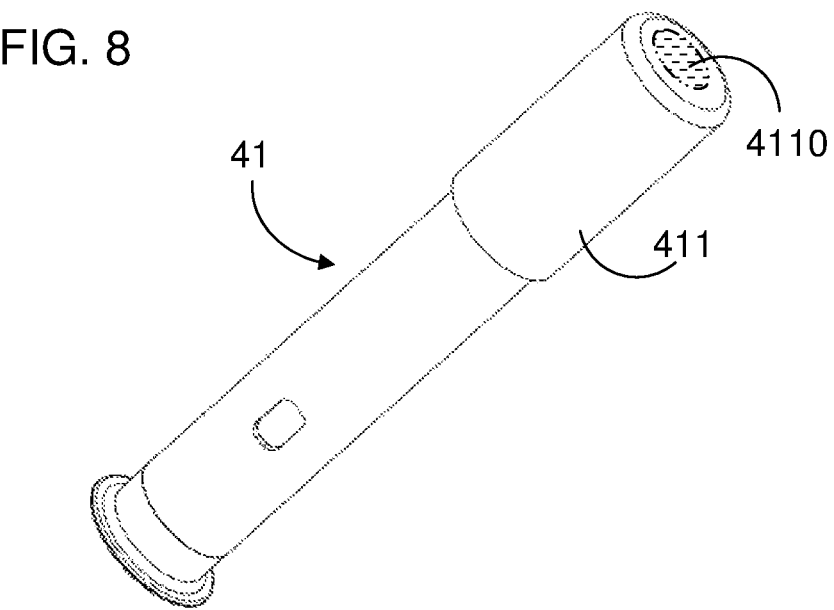
FIGS. 8 and 9 illustrate example RFID enabled or NFC-enabled dose drug delivery devices.
Figure 9:
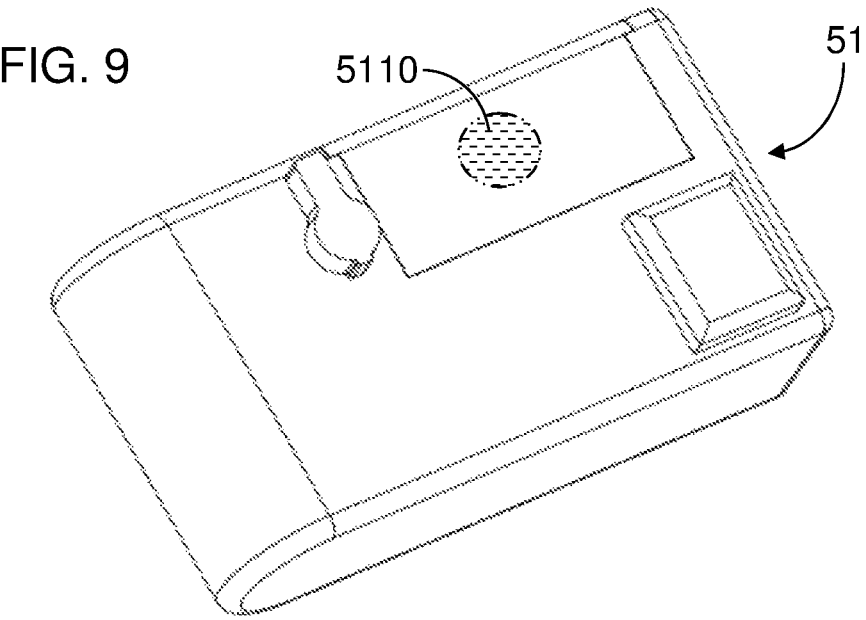

FIGS. 8 and 9 illustrate examples variable dose drug delivery devices with embedded RFID tag or NFC tag. In FIG. 8, the variable dose autoinjector device 41 has a top cap 411. The RFID tag (or NFC tag) 4110 is embedded in the top cap 411. The device 41 has the same design and operation procedure to the device 40. In FIG. 9, the variable dose infusor device 51 has a housing cover 511. The NFC tag (or RFID tag) 5110 is embedded in the housing cover 511. The device 51 has the same design and operation procedure to the device 50.

FIG. 10 illustrates a block diagram of example method 90 configured to improve patient adherence during clinical trial, according to this invention. The method 90 is to utilize NFC-enabled or RFID-enable device(s) to remind, record and assess the drug self-administration, as well as track storage information during clinical trial. The method 90 starts with operation 901 where radio frequency identification (RFID) tag or near field communication (NFC) tag are embedded into component of the variable dose drug delivery device(s) used in this invention, for example, by insert molding. At operation 902, medicine and medicine dosage information are written to RFID or NFC tag. At operation 903, medicine, dosing schedule, dosage, as well as storage requirement are written into RFID or NFC enabled device. This is normally accomplished by pre-installing software (or mobile App) on the RFID or NFC enabled device. At operation 904, based on dosing schedule, RFID or NFC enabled device generate alert to remind user for drug administration according to the pre-installed dosing schedule. Once the user is alerted, he/she needs to bring the variable dose drug delivery device close to the RFID or NFC enabled device and lets the RFID or NFC enabled device to read the tag embedded in the variable dose drug delivery device (operation 905). User checks whether medicine and dose stored in the RFID or NFC tag are correct (operation 906). User can also optionally check whether the storage environment is correct for the parenteral medicine during this time. If all the information are correct, the alert can be disable and user can conduct the drug administration (operation 906). If any information isn't correct, the alert will be continued (operation 907) or a different alert will be generated. With this method, the patient adherence can be greatly improved.

All the steps and features in the above embodiments and concepts herein can be inter-changed and combined to generate new method. Those of skill in the art will understand that modifications (additions and/or removals) of various steps of the methods, components of the apparatuses, and/or systems and embodiments described herein may be made without departing from the full scope and spirit of the present invention, which encompass such modifications and any and all equivalents thereof.

The invention claimed is:

1. A method of conducting an adaptive clinical trial for developing a therapeutic product, the method comprising:
    Preparing a plurality of single-use variable dose automatic drug delivery devices, each single-use variable dose automatic drug delivery device is loaded with a predetermined maximum dose of the therapeutic product and a dose setting element configured to adjust a plurality of discrete delivery volumes of the therapeutic product, the plurality of single-use variable dose automatic drug delivery devices including at least a first, a second, a third, and a fourth automatic drug delivery device;
    Enrolling a first patient and a second patient into the adaptive clinical trial;
    Delivering, by the first single-use variable dose automatic drug delivery device, a first delivery volume of the therapeutic product to the first patient enrolled in the adaptive clinical trial;
    Delivering, by the second single-use variable dose automatic drug delivery device, a second delivery volume of the therapeutic product to the second patient enrolled in the adaptive clinical trial, wherein the second delivery volume of the therapeutic product is different from the first delivery volume of the therapeutic product, and wherein the difference between the first delivery volume of the therapeutic product and the second delivery volume of the therapeutic product is blinded to the first patient and the second patient enrolled in the adaptive clinical trial;
    Collecting and analyzing therapeutic product response data for the first and second patients in real time;
    Adjusting the dose setting element of the third and fourth single-use variable automatic drug delivery devices based on the therapeutic product response data for each patient;
    Repeating the steps of delivering the therapeutic product and adjusting the dose volume until the clinical trial goal is reached.

2. The method of claim 1, wherein delivering, by the first single-use variable dose automatic drug delivery device, the first delivery volume of the therapeutic product to the first patient enrolled in the adaptive clinical trial is based on the first patient's individual characteristic, wherein the first patient's individual characteristic is disease stage, genetic makeup, weight, age, gender, diet information, lifestyle, or metabolize rate.

3. The method of claim 1, wherein delivering, by the second single-use variable dose automatic drug delivery device, the second delivery volume of the therapeutic product to the second patient enrolled in the adaptive clinical trial is based on the second patient's individual characteristic, wherein the second patient's individual characteristic is disease stage, genetic makeup, weight, age, gender, diet information, lifestyle, or metabolize rate.

4. The method of claim 1, wherein the plurality of single-use variable dose automatic drug delivery devices are a variable dose autoinjector or a variable dose infusor.

5. The method of claim 1, wherein analyzing therapeutic product response data for the first and second patients is with using a modeling approach, wherein the modeling approach is pharmacokinetics/pharmacodynamics modeling, toxicology modeling, statistical modeling or machine learning.

6. A method of conducting an adaptive clinical trial for developing a therapeutic product, the method comprising:
Preparing a plurality of single-use variable dose automatic drug delivery devices, each single-use variable dose automatic drug delivery device is loaded with a predetermined maximum dose of the therapeutic product and further including a dose setting element configured to adjust a plurality of discrete delivery volumes of the therapeutic product, the plurality of single-use variable dose automatic drug delivery devices including at least a first, and a second automatic drug delivery device;
Enrolling a patient into the adaptive clinical trial;
Delivering, by the first single-use variable dose automatic drug delivery device, a first delivery volume of the therapeutic product to the patient enrolled in the adaptive clinical trial;
Collecting and analyzing the patient's response to the first delivery volume of the therapeutic product in real time;
Adjusting the dose setting element of the second single-use variable automatic drug delivery devices based on the therapeutic product response data for the patient;
Delivering, by the second single-use variable dose drug delivery device, a second delivery volume of the therapeutic product to the patient enrolled in the adaptive clinical trial, wherein the second delivery volume of the therapeutic product is different from the first delivery volume of the therapeutic product, and wherein the difference between the first delivery volume of the therapeutic product and the second delivery volume of the therapeutic product is blinded to the patient enrolled in the adaptive clinical trial; and
Repeating the steps of delivering the therapeutic product and adjusting the dose volume until the clinical trial goal is reached.

7. The method of claim 6, wherein delivering, by the first single-use variable dose automatic drug delivery device, the first delivery volume of the therapeutic product to the patient enrolled in the adaptive clinical trial is based on the patient's individual characteristic, wherein the patient's individual characteristic is disease stage, genetic makeup, weight, age, gender, diet information, lifestyle, or metabolize rate.

8. The method of claim 6, wherein delivering, by the second single-use variable dose automatic drug delivery device, the second delivery volume of the therapeutic product to the patient enrolled in the adaptive clinical trial is based on the patient's response to the first delivery volume of the therapeutic product and the patient's individual characteristic, wherein the patient's individual characteristic is disease stage, genetic makeup, weight, age, gender, diet information, lifestyle, or metabolize rate.

9. The method of claim 6, wherein analyzing the patient's response to the first delivery volume of the therapeutic product is with using a modeling approach, wherein the modeling approach is pharmacokinetics/pharmacodynamics modeling, toxicology modeling, statistical modeling or machine learning.

10. The method of claim 6, wherein the plurality of single-use variable dose automatic drug delivery devices are a variable dose autoinjector or a variable dose infusor.

11. A method of conducting an adaptive clinical trial for developing a therapeutic product, the method comprising:
Preparing a plurality of single-use variable dose automatic drug delivery devices, each single-use variable dose automatic delivery device is loaded with a predetermined maximum dose of the therapeutic product, an embedded communication component and a dose setting element configured to adjust a plurality of discrete delivery volumes of the therapeutic product, the plurality of single-use variable dose automatic drug delivery devices including at least a first, and a second automatic drug delivery device;
Enrolling a patient into the adaptive clinical trial;
Writing information of a first delivery volume of the therapeutic product into a communication component embedded in the first single-use variable dose automatic drug delivery device;
Delivering, by the first single-use variable dose automatic drug delivery device, the first delivery volume of the therapeutic product to the patient enrolled in the adaptive clinical trial;
Collecting and analyzing therapeutic product response data for the patient in real time;
Adjusting the dose setting element of the second single-use variable automatic drug delivery device based on the therapeutic product response data for the patient;
Writing information of a second delivery volume of the therapeutic product into a communication component embedded in the second single-use variable automatic dose drug delivery device;
Delivering, by the second single-use variable dose drug delivery device, the second delivery volume of the therapeutic product to the patient enrolled in the adaptive clinical trial, wherein the second delivery volume of the therapeutic product is different from the first delivery volume of the therapeutic product, and wherein the difference between the first delivery volume of the therapeutic product and the second delivery volume of the therapeutic product is blinded to the patient enrolled in the adaptive clinical trial but is distinguishable by retrieving the information of the first delivery volume of the therapeutic product and the second delivery volume of the therapeutic product written in the communication components embedded in the first and second single-use variable drug delivery device; and
Repeating the steps of delivering the therapeutic product, adjusting the dose volume, and writing information of the delivery volume until the clinical trial goal is reached.

12. The method of claim 11, wherein retrieving the information of the first delivery volume of the therapeutic product and the second delivery volume of the therapeutic product written in the communication components embedded in the first and second single-use variable dose automatic drug delivery device is wireless.

13. The method of claim 12, wherein the communication component is radio frequency identification (RFID) tag, near field communication (NFC) tag, or bluetooth communication chip.

14. The method of claim 11, wherein the plurality of single-use variable dose automatic drug delivery devices are a variable dose autoinjector or a variable dose infusor.

15. The method of claim 11, wherein the second single-use variable dose automatic drug delivery device is used before a predetermined period elapses after the first single-use variable dose automatic drug delivery device is used.

16. The method of claim 15, wherein the second single-use variable dose automatic drug delivery device is able to issue an alert if the predetermined period elapses after the first single use variable dose automatic drug delivery device is used.

17. The method of claim 11, further comprising the step of recording information of storage condition of the first and second single-use variable dose automatic drug delivery devices loaded with the therapeutic product into the communication components embedded in the first and second single-use variable dose automatic drug delivery device.

18. The method of claim 11, wherein analyzing therapeutic product response data for the patient is with using a modeling approach, wherein the modeling approach is pharmacokinetics/pharmacodynamics modeling, toxicology modeling, statistical modeling or machine learning.

* * * * *